(12) United States Patent
Ohtsubo

(10) Patent No.: US 10,980,678 B2
(45) Date of Patent: Apr. 20, 2021

(54) STRETCHABLE AND CONTRACTIBLE SHEET AND ABSORBENT ARTICLE

(71) Applicant: UNICHARM Corporation, Ehime (JP)

(72) Inventor: Toshifumi Ohtsubo, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/752,031

(22) Filed: Jan. 24, 2020

(65) Prior Publication Data

US 2020/0155370 A1 May 21, 2020

Related U.S. Application Data

(63) Continuation of application No. PCT/JP2018/036262, filed on Sep. 28, 2018.

(30) Foreign Application Priority Data

Oct. 4, 2017 (JP) .............................. JP2017-194553

(51) Int. Cl.
*A61F 13/15* (2006.01)
*A61F 13/49* (2006.01)
(Continued)

(52) U.S. Cl.
CPC .. *A61F 13/49019* (2013.01); *A61F 13/49014* (2013.01); *B32B 5/022* (2013.01);
(Continued)

(58) Field of Classification Search
CPC .......... A61F 13/49019; A61F 13/49014; A61F 13/496; A61F 13/51; A61F 2013/49093;
(Continued)

(56) References Cited

U.S. PATENT DOCUMENTS 5,626,574 A * 5/1997 Sasaki ................. B29C 66/1122
604/385.29
2004/0133180 A1 7/2004 Mori et al.
(Continued)

FOREIGN PATENT DOCUMENTS

EP 1666178 A1 6/2006
EP 2801344 * 5/2014 ............. A61F 13/49
(Continued)

OTHER PUBLICATIONS

International Preliminary Report on Patentability issued in corresponding International Application No. PCT/JP2018/036262, dated Apr. 8, 2020, with translation (8 pages).
(Continued)

*Primary Examiner* — Jacqueline F Stephens
(74) *Attorney, Agent, or Firm* — Osha Bergman Watanabe & Burton LLP

(57) ABSTRACT

A stretchable/contractible sheet having an up-down direction and a left-right direction intersecting each other is provided. The stretchable and contractible sheet includes: a first welded-portion row including a plurality of welded portions arranged side-by-side in the up-down direction; and a second welded-portion row including the plurality of welded portions located adjacent to the first welded-portion row on a one side in the left-right direction. The first welded-portion row includes: a first convex portion protruding toward the one side; and a second convex portion. The second welded-portion row includes a third convex portion protruding toward another side opposite to the one side in the left-right direction.

15 Claims, 8 Drawing Sheets

(51) Int. Cl.
  *B32B 7/05* (2019.01)
  *B32B 5/02* (2006.01)
  *B32B 27/12* (2006.01)
  *B32B 27/32* (2006.01)
  *A61F 13/496* (2006.01)

(52) U.S. Cl.
  CPC ............ *B32B 7/05* (2019.01); *B32B 27/12* (2013.01); *B32B 27/32* (2013.01); *A61F 13/496* (2013.01); *A61F 2013/49093* (2013.01); *B32B 2307/51* (2013.01); *B32B 2307/726* (2013.01); *B32B 2555/02* (2013.01)

(58) Field of Classification Search
  CPC ........ B32B 5/022; B32B 27/32; D04H 1/559; D04H 1/74
  See application file for complete search history.

(56) References Cited

U.S. PATENT DOCUMENTS

| | | | |
|---|---|---|---|
| 2016/0058627 A1* | 3/2016 | Barnes | A61F 13/5655 604/385.3 |
| 2017/0049639 A1* | 2/2017 | Shimazu | A61F 13/49058 |

FOREIGN PATENT DOCUMENTS

| | | |
|---|---|---|
| JP | 2001-504899 A | 4/2001 |
| JP | 2008-154998 A | 7/2008 |
| JP | 2012-217553 A | 11/2012 |
| JP | 6171120 B1 | 7/2017 |
| WO | 2019148156 A1 | 8/2019 |

OTHER PUBLICATIONS

International Search Report issued in corresponding International Application No. PCT/JP2018/036262 dated Nov. 13, 2018 (3 pages).
Written Opinion of the International Searching Authority issued in corresponding International Application No. PCT/JP2018/036262 dated Nov. 13, 2018 (4 pages).
Extended European Seach Report issued in the counterpart European Patent Application No. 18865016.2, dated Oct. 29, 2020 (8 pages).
Examination Report issued in corresponding GCC Application No. GC2018-36155 dated Feb. 1, 2021 (7 pages).

* cited by examiner

STRETCHABLE AND CONTRACTIBLE SHEET AND ABSORBENT ARTICLE

CROSS-REFERENCE TO RELATED APPLICATIONS

This application is based on and claims priority under 35 U.S.C. § 119 from Japanese Patent Application No. 2017-194553 filed on Oct. 4, 2017, the contents of which are incorporated herein by reference.

TECHNICAL FIELD

The present invention generally relates to a stretchable and contractible sheet and an absorbent article.

BACKGROUND

As an example of an absorbent article that absorbs excrement such as urine, a disposable diaper is known. As a waist member of a disposable diaper, a sheet member is generally employed to which stretch/contraction ability is applied by attaching elastic members thereto with adhesive such as hot-melt adhesive. But, in the case where the elastic members are attached with adhesive, curing of the adhesive attached onto the outer surface of elastic members causes a risk of deterioration of elasticity of the elastic members, that is stretch/contraction ability, and/or causes a risk of deterioration of flexibility of the sheet member. Therefore, attaching elastic members to a sheet member without adhesive is recently considered.

For example, wire-like elements capable of elastically stretching are arranged between two sheet members stacked in the thickness direction while the wire-like elements are stretched in the lengthwise direction. Furthermore, the two sheet members are joined with a plurality of joints which are formed by means such as welding means. When the wire-like elements are released from the stretched state and contract in the lengthwise direction so that the outer diameter is thicker, each wire-like element is sandwiched by a pair of joints arranged on both sides in the radial direction of the wire-like element, fixing the wire-like elements between the sheet members. There is disclosed such a technique for manufacturing a sheet member having a stretch/contraction ability without adhesive, which is applied to an absorbent article such as a napkin or a diaper (see PTL 1).

PATENT LITERATURE

[PTL 1] Japanese Unexamined Patent Application Publication (Translation of PCT Application) No. 2001-504899

In the stretchable/contractible sheet member of PTL 1, joining portions (welded portions) are formed along the lengthwise direction of the wire-like elements at regular intervals. Accordingly, accompanying with the contraction of the wire-like elements (elastic members), regular creases are more likely to be formed on the surface of the sheet member. Specifically, long creases continuing in a direction perpendicular to the lengthwise direction of the wire-like elements are formed with spacing along the lengthwise direction. In an absorbent article (e.g., a diaper) which is manufactured using such a sheet member, large creases are formed regularly on the surface of the sheet member. This makes it easier for large creases to mark the wearer's skin when the absorbent article canes into contact with wearer's body (skin). Consequently, it is difficult to realize good touch.

SUMMARY

One or more embodiments provide a stretchable and contractible sheet that has a flexibility and which may enable to have irregular, fine creases formed on its surface.

One or more embodiments provide a stretchable and contractible sheet. The stretchable and contractible sheet comprises:
a first sheet;
a second sheet;
a plurality of welded portions joining the first sheet and the second sheet;
a plurality of elastic members being capable of stretching/contracting in the left-right direction,
   the plurality of elastic members arranged with a space in the up-down direction and between the first sheet and the second sheet that are joined by the plurality of welded portions, and
   each of the elastic members being sandwiched between two welded portions adjacent in the up-down direction with contracting in the left-right direction, and being attached to the first sheet and the second sheet;
a first welded-portion row including a plurality of the welded portions arranged side-by-side in the up-down direction; and
a second welded-portion row including a plurality of the welded portions arranged side-by-side in the up-down direction, and located adjacent to the first welded-portion row on a one side in the left-right direction,
   the first welded-portion row including
      a first convex portion that projects toward the one side in the left-right direction, and
      a second convex portion located adjacent to the first convex portion in the up-down direction,
   the second welded-portion row including a third convex portion that projects toward another side in the left-right direction,
in a natural state,
   an other-side end of the third convex portion being located on the other side with respect to a straight line connecting a one-side end of the first convex portion and a one-side end of the second convex portion.

Features of one or more embodiments will become apparent from the description in this specification and the attached drawings.

According to one or more embodiments, it is possible to a stretchable/contractible sheet that has a flexibility and which may enable to have irregular, fine creases formed on its surface.

DETAILED DESCRIPTION

Figure 1:
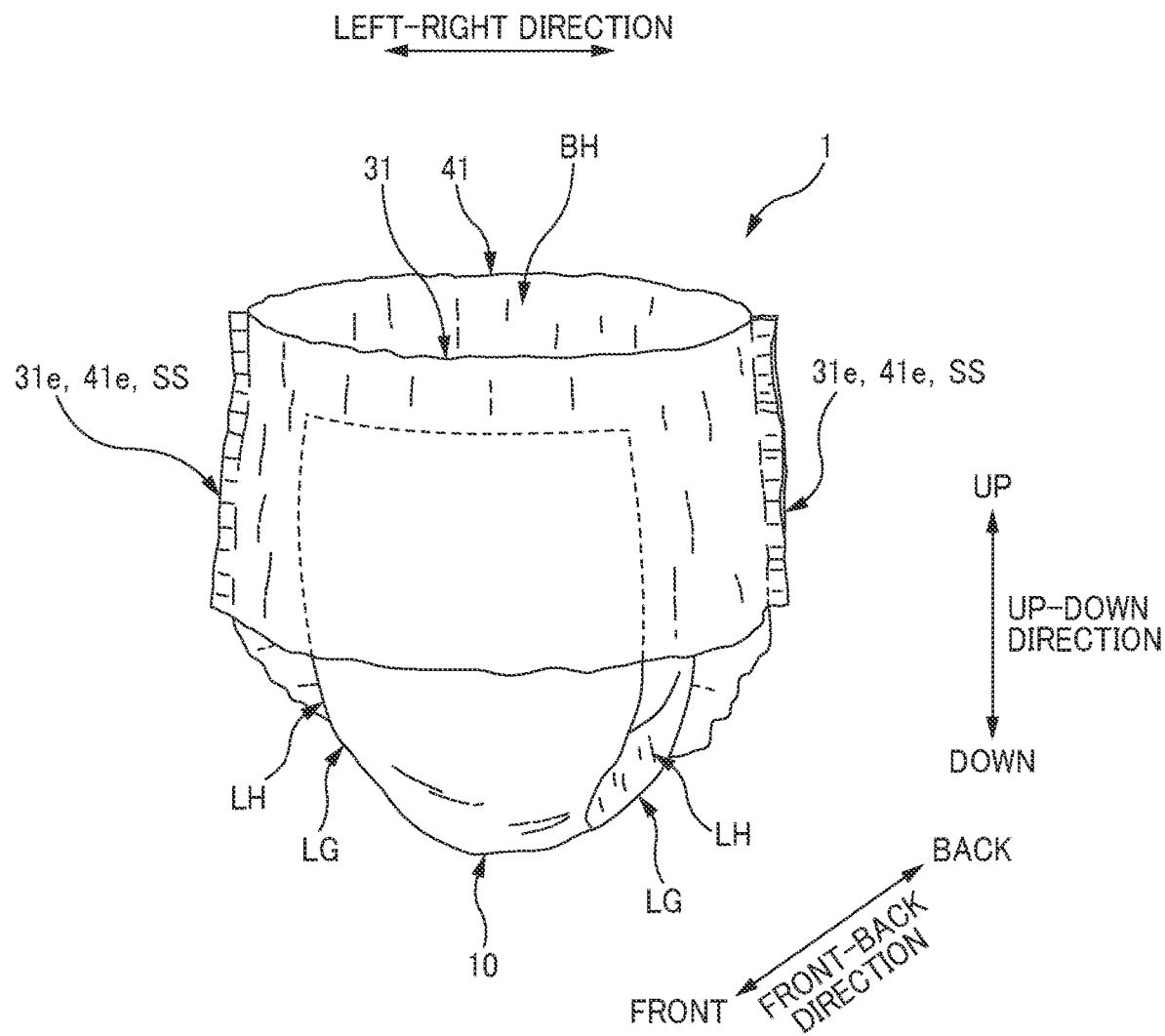
FIG. 1 shows a schematic perspective view of a diaper 1 according to one or more embodiments.

At least the following matters will be made clear by the description in the present specification and the accompanying drawings.

A stretchable/contractible sheets having an up-down direction and a left-right direction intersecting each other,
the stretchable/contractible sheet, including:
a first sheet;
a second sheet;
a plurality of welded portions joining the first sheet and the second sheet;
a plurality of elastic members being capable of stretching/ contracting in the left-right direction,
the plurality of elastic members arranged with a space in the up-down direction and between the first sheet and the second sheet that are joined by the plurality of welded portions, and
each of the elastic members being sandwiched between two welded portions adjacent in the up-down direction with contracting in the left-right direction, and being attached to the first sheet and the second sheet;
a first welded-portion row including the plurality of welded portions arranged side-by-side in the up-down direction; and
a second welded-portion row including the plurality of welded portions arranged side-by-side in the up-down direction, and located adjacent to the first welded-portion row on a one side in the left-right direction,
the first welded-portion row including
a first convex portion that protrudes toward the one side in the left-right direction, and
a second convex portion located adjacent to the first convex portion in the up-down direction,
the second welded-portion row including a third convex portion that protrudes toward another side in the left-right direction,
in a natural state,
an other-side end of the third convex portion being located on the other side with respect to a straight line connecting a one-side end of the first convex portion and a one-side end of the second convex portion.

With such a stretchable/contractible sheet, since the welded portions are formed discretely, it is possible to realize a flexible sheet member whose deformation in the up-down direction and the left-right direction is less likely to be suppressed. In natural state, irregular fine creases are more likely to be formed between the convex portions of the welded-portion row. Accordingly, compared to the case where long, continuous, and straight creases are formed, it is possible for the touch on the surface of the sheet member to be softer. In a portion where such fine creases are formed, the basis weight of the sheet member is locally large, increasing cushioning. This makes it possible to realize better touch.

In such a stretchable/contractible sheet,
in a state where the stretchable/contractible sheet is stretched in the left-right direction,
the other-side end of the third convex portion is located on the one side with respect to the straight line connecting the one-side end of the first convex portion and the one-side end of the second convex portion.

With such a stretchable/contractible sheet, accompanying with contraction of the elastic members, the other-side end of the third convex portion moves from the other side to the one side with respect to the straight line connecting the one-side end of the first convex portion and the one-side end of the second convex portion. This makes it possible to form creases in a region corresponding to the distance of the foregoing movement. Furthermore, creases curved in the left-right direction along the convex portions are formed. Since the directions of creases differ, creases are easier to break and shorten, making it easier to form discrete fine creases in the up-down direction. This makes it possible for the touch on the surface of the sheet member to be softer.

In such a stretchable/contractible sheet,
of the plurality of welded portions included in the first welded-portion row and the second welded-portion row,
each pair of two welded portions adjacent in the up-down direction has a portion overlapping in the left-right direction.

With such a stretchable/contractible sheet, concerning each pair of two welded portions adjacent in the up-down direction, its displacement in the left-right direction is smaller than the length of the welded portion in the left-right direction. That is, restricting the displacement of the welded portion within a predetermined range makes smooth the convex portions and the concave portions of the welded-portion row in the left-right direction. Curved, fine creases become more likely to be formed between the convex portions. This makes it possible for the touch on the surface of the sheet to be soft.

In such a stretchable/contractible sheet,
a length of the portion that is included in the two welded portions adjacent in the up-down direction and in which the two welded portions overlap in the left-right direction
is larger than
a length of a portion that is included in the two welded portions and in which the two welded portions do not overlap in the left-right direction.

With such a stretchable/contractible sheet, the length of the left-right-direction overlapping portion of the welded portions is larger than half the length of the welded portion in the left-right direction. This prevents the left-right-direction amplitude of the convex portions and the concave portions of the welded-portion row from being excessively large, making it further easier to form curved, fine creases in regions between the convex portions. This makes it easier to realize softer touch.

In such a stretchable/contractible sheet,
the welded-portion row extends downward in the up-down direction and meanders in the left-right direction.

With such a stretchable/contractible sheet, it becomes easier to form curved fine creases. Also, since the welded-portion row itself forms a curved geometric pattern on the stretchable/contractible sheet, appearance design thereof can improve.

In such a stretchable/contractible sheet,
a length of the welded portion in the left-right direction is larger than a length of the welded portion in the up-down direction.

With such a stretchable/contractible sheet, since the shape of the welded portion is laterally elongated, this increases the area (length) of a portion in which the elastic member and the welded portion are in contact with each other in the left-right direction. Accordingly, friction force produced in the contact portion can increase. This makes it difficult to cause displacement of the elastic members fixed by the welded portions, and the stretchable/contractible sheet can have a reliable stretch/contraction ability.

In such a stretchable/contractible sheet,
a length of the welded portion in the up-down direction is larger than an up-down-direction space of two adjacent welded portions.

With such a stretchable/contractible sheet, formed is a welded-portion row which does not have a large break in the up-down direction. Accordingly, between adjacent welded-portion rows, distortion is less likely to be produced on the surface of the sheet when the stretchable/contractible sheet contracts in the left-right direction. This makes it easier to form creases along convex portions and concave portions (curves) of the welded-portion row, enabling to realize good touch.

In such a stretchable/contractible sheet,
the plurality of elastic members includes a first elastic member and a second elastic member adjacent to the first elastic member in the up-down direction, and
a space in the up-down direction between the first elastic member and the second elastic member is smaller than a space in the up-down direction between the one-side end of the first convex portion and the one-side end of the second convex portion.

With such a stretchable/contractible sheet, the up-down-direction space of the elastic members are smaller than the space between the convex portions adjacent in the up-down direction. This may enable contraction force caused by the elastic members to be reliably exerted on a region between the convex portions, making it easier to form creases. This makes it easier to realize good touch.

In such a stretchable/contractible sheet,
the plurality of elastic members includes the first elastic member and the second elastic member adjacent to the first elastic member in the up-down direction, and
the space in the up-down direction between the first elastic member and the second elastic member is smaller than half the space in the up-down direction between the one-side end of the first convex portion and the one-side end of the second convex portion.

With such a stretchable/contractible sheet, the elastic members exert a greater per-unit-are contraction force on a region between two convex portions adjacent in the up-down direction. This can make it further easier to form creases.

In such a stretchable/contractible sheet,
the elastic members are attached at a stretching ratio that produces a contraction force being capable of moving the other-side end of the third convex portion
so that, in a state where the stretchable/contractible sheet is stretched in the left-right direction,
the other-side end of the third convex portion is located on the one side with respect to the straight line connecting the one-side end of the first convex portion and the one-side end of the second convex portion, and
so that, in the natural state,
the other-side end of the third convex portion is located on the other side with respect to the straight line connecting the one-side end of the first convex portion and the one-side end of the second convex portion.

With such a stretchable/contractible sheet, contraction of the elastic members can move the position of the other-side end of the third convex portion to the other side with respect to the straight line connecting the one-side end of the first convex portion and the one-side end of the second convex portion. This suppresses formation of long and continuous creases in a region between the third convex portion and the first convex portion (the second convex portion), making it easier to form irregular fine creases.

In such a stretchable/contractible sheet,
the elastic member is attached at a stretching ratio not less than twice and not more than third times.

With such a stretchable/contractible sheet, the position of the other-side end of the third convex portion can move to the other side with respect to the straight line connecting the one-side end of the first convex portion and the one-side end of the second convex portion. In addition, it is possible to suppress excessive tightening force which is produced when excessively great contraction force is exerted on the absorbent article.

In such a stretchable/contractible sheet,
in the left-right direction, a space of two adjacent welded portions is equal to or less than 6 mm.

With such a stretchable/contractible sheet, in the natural state, the position of the other-side end of the third convex portion is easier to move to the other side with respect to the straight line connecting the one-side end of the first convex portion and the one-side end of the second convex portion. This makes it easier to form irregular, fine creases on the surface of the stretchable/contractible sheet.

An absorbent article having an up-down direction and a left-right direction intersecting each other, including:
an absorbent main body that absorbs excrement;
a front band member provided along the left-right direction and joined to a front-upper-end portion of the absorbent main body;
a back band member provided along the left-right direction separately from the front band member, and joined to a back-upper-end portion of the absorbent main body;
the front band member and the back band member including:
a first sheet;
a second sheet;
a plurality of welded portions joining the first sheet and the second sheet;
a plurality of elastic members being capable of stretching/contracting in the left-right direction, the plurality of elastic members arranged with a space in the up-down direction and between the first sheet and the second sheet,
each of the elastic members being sandwiched between two welded portions adjacent in the up-down direction with contracting in the left-right direction, and being attached to the first sheet and the second sheet;
a first welded-portion row including the plurality of welded portions arranged side-by-side in the up-down direction; and
a second welded-portion row including the plurality of welded portions arranged side-by-side in the up-down direction, and located adjacent to the first welded-portion row on a one side in the left-right direction,
the first welded-portion row including
a first convex portion that protrudes toward the one side in the left-right direction, and
a second convex portion located adjacent to the first convex portion in the up-down direction,
the second welded-portion row including a third convex portion that protrudes toward another side in the left-right direction,
in a natural state,
an other-side end of the third convex portion being located on the other side with respect to a straight line connecting a one-side end of the first convex portion and a one-side end of the second convex portion.

With such an absorbent article, it is possible to realize good touch and/or good fit in the front (back) band member which is to be in contact with the wearer's waist. Also, on the surface of the band members, curved creases are formed which are less likely to fall and crush compared to straight creases. This makes it easier to keep good fit and/or good touch when the absorbent article is put on.

In such an absorbent article,
in the up-down direction,
a space of the elastic members disposed in the front band member is different from a space of the elastic members disposed in the back band member.

With such an absorbent article, the size and the shape of creases formed on each surface can be different between the front band member and the back band member. Accordingly, the front band member and the back band member are less likely to be in close contact in the thickness direction. This can make it easier to open the front band member and the back band member in the front-back direction to form a waist opening when putting on the absorbent article.

In such an absorbent article,
in the up-down direction,
a space of the elastic members disposed in the front band member is smaller than a space of the elastic members disposed in the back band member.

With such an absorbent article, in the back band member in which the pitch between the elastic members in the up-down direction is large, it can be easier to form creases having large inclinations. By the amount the inclinations of creases are large, the back band member has a longer elongation in the up-down direction than that of the front band member. Consequently, when putting on the absorbent article, the back band member becomes easy to stretch in the up-down direction. Accordingly, in the region of buttocks whose movement is large, the back band member becomes more likely to follow the wearer's body movement, improving fit.

<Configuration of Disposable Diaper>

Figure 2:
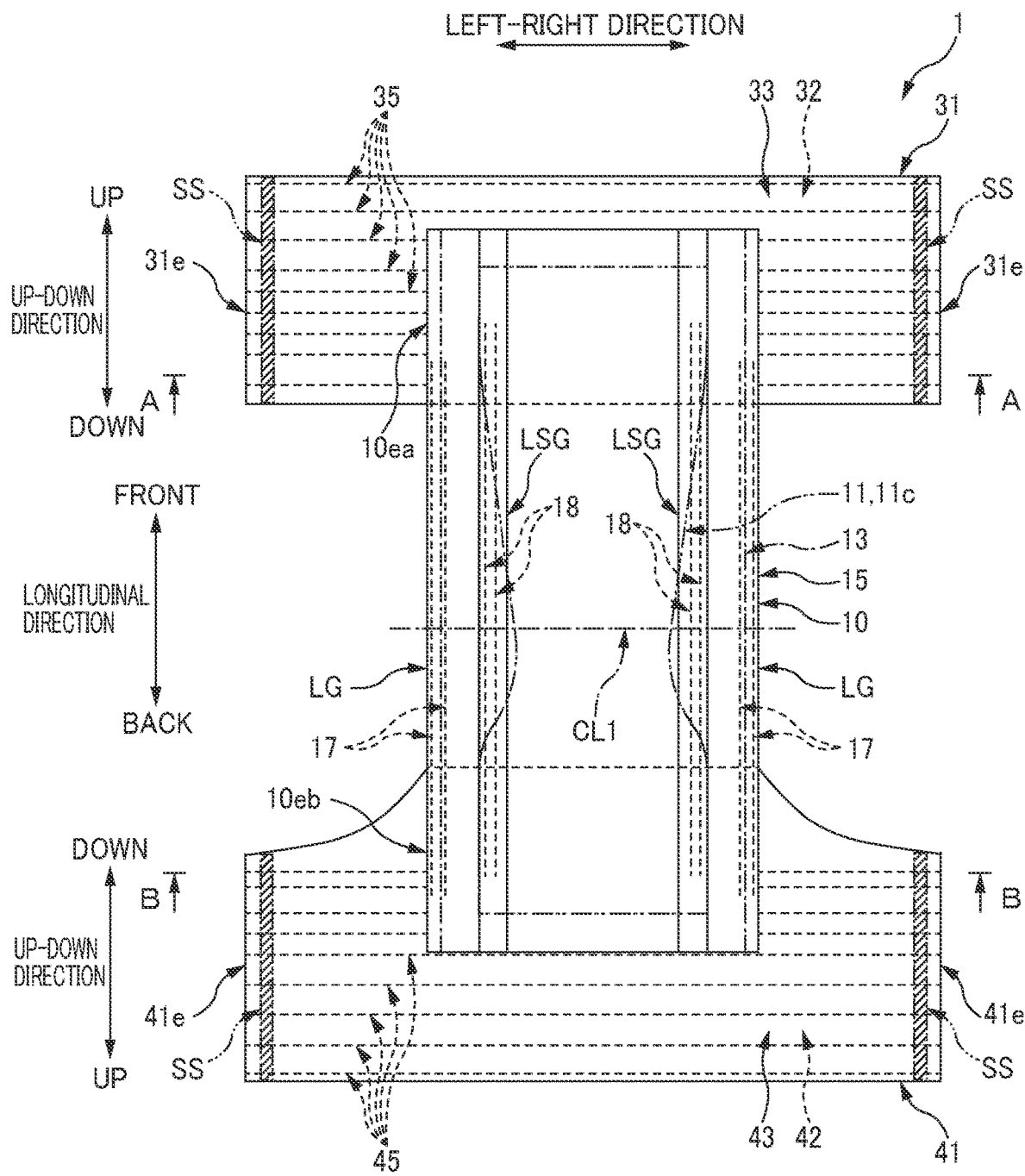
FIG. 2 shows a schematic plan view of a diaper 1 which is opened and stretched, as viewed from the skin side of a wearer according to one or more embodiments.
Figure 3:
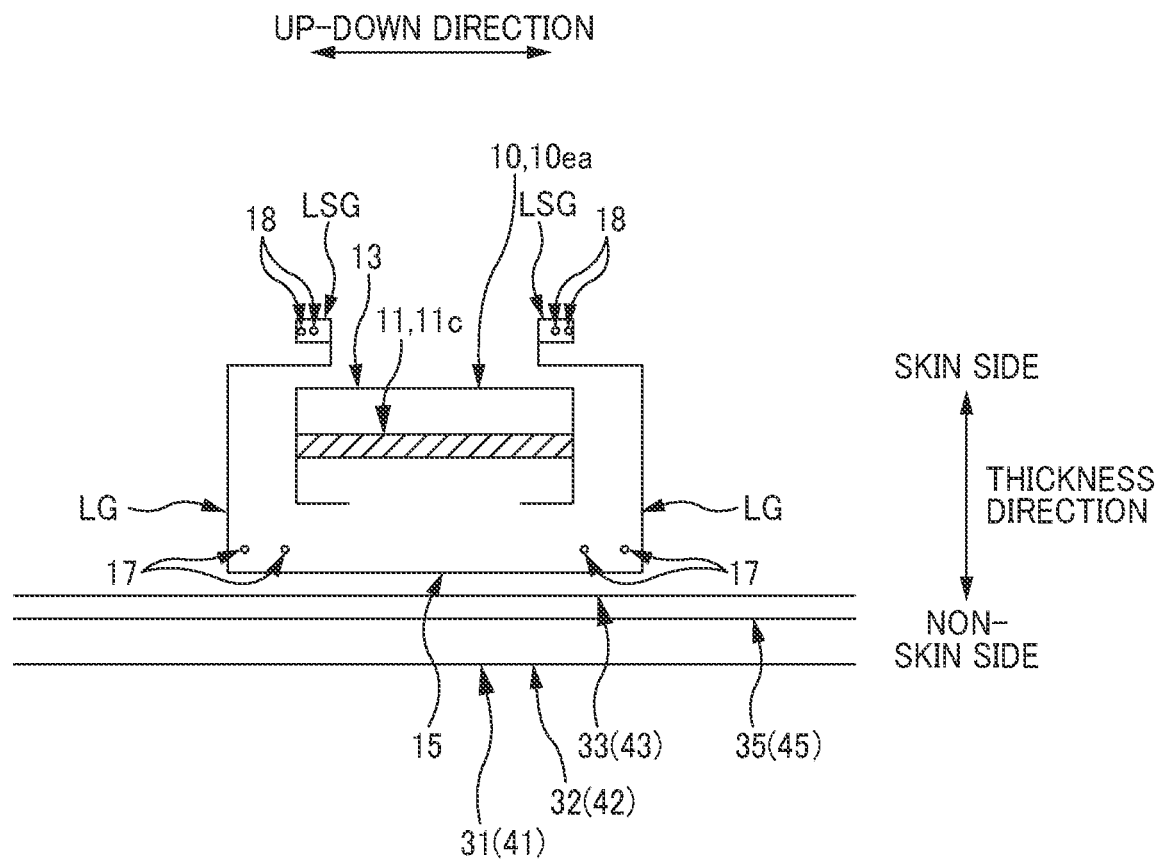
FIG. 3 shows a diagram illustrating the structure of an absorbent main body 10 according to one or more embodiments.

An absorbent article to which a stretchable/contractible (stretchable and contractible) sheet according to one or more embodiments is applied is exemplified by a disposable diaper 1 (hereinafter referred to as a "diaper 1"), and it will be described below. In the diaper 1, a stretchable/contractible sheet is used as waist band members (a front band member 31 and a back band member 41; to be described later). FIG. 1 is a schematic perspective view of a diaper 1. FIG. 2 is a schematic plan view of the diaper 1 which is opened and stretched, as viewed from the skin side of a wearer. FIG. 3 is a cross-sectional view taken along line A-A in FIG. 2, and is also a cross-sectional view taken along line B-B in FIG. 2.

When the diaper 1 is in a state where it has a pants shape before it is worn shown in FIG. 1, the diaper 1 has: an "up-down direction"; a "left-right direction" perpendicular to the up-down direction; and a "front-back direction" perpendicular to the up-down direction and the left-right direction. In the up-down direction, the upper side corresponds to the waist opening side for a wearer, and the lower side corresponds to the wearer's crotch side. In the front-back direction, the front side corresponds to the side of a wearer's front, and the back side corresponds to the side of a wearer's back.

When the diaper 1 is in a pants shape shown in FIG. 1, the diaper 1 includes: a front band member 31 that has a stretch/contraction ability along the left-right direction; a back band member 41 which is located back the front band member 31 and which has a stretch/contraction ability along the left-right direction for forming a waist opening BH on the up side in the up-down direction in cooperation with the front band member 31; and an absorbent main body 10 disposed between the front band member 31 and the back band member 41 as a crotch portion. The absorbent main body 10 is located protruding downward in the up-down direction beyond the front band member 31 and the back band member 41.

In the left-right direction, the end portions 31e and 31e of the front band member 31 are joined with the corresponding end portions 41e and 41e of the back band member 41 by a side seal portion SS serving as a welded portion. Thus, the front band member 31 and the back band member 41 form, together with the absorbent main body 10, a leg opening LH on each side in the left-right direction and on the underside.

An "opened state" of the diaper 1 is a state in which the pants-shaped diaper 1 in FIG. 1 is opened on a plane by separating the front band member 31 and the back band member 41 by unjoining the joining of foregoing side seal portions SS on both sides in the left-right direction, and by opening the diaper 1 in the up-down direction. A "stretched state" is a state in which a product (the diaper 1) is stretched without creases, specifically, according to one or more embodiments, it is a state in which members constituting the diaper 1 (e.g., the absorbent main body 10 and the front band member 31) are stretched until the length of each member becomes substantially equal to its original length.

In the opened state, the diaper 1 has three directions perpendicular to one another: the longitudinal direction; the left-right direction; and the thickness direction (a direction penetrating the paper plane of FIG. 2). The longitudinal direction extends along the foregoing up-down direction. The one side of the longitudinal direction corresponds to the front side, and the other side corresponds to the back side. The outer side in the longitudinal direction corresponds to the up side in the up-down direction (the waist opening side), and the inner side in the longitudinal direction corresponds to the down side in the up-down direction (crotch side). Thus, since the longitudinal direction and the up-down direction are similar to each other, the following description related to the opened state will sometimes be made using the up-down direction instead of the longitudinal direction for the purpose of explanation. Meanwhile, the left-right direction in the opened state is identical to the left-right direction in the foregoing pants-shaped diaper. In the thickness direction, the one side corresponds to the skin side which is in contact with a wearer's body, and the other side corresponds to the non-skin side, which is opposite thereto. The thickness direction extends along the foregoing front-back direction.

In the opened state in FIG. 2, the front band member 31 is placed along the left-right direction, and the back band member 41 is placed along the left-right direction, with a certain longitudinal space from the front band member 31. The absorbent main body 10 is placed along the longitudinal direction between the front band member 31 and the back band member 41. Furthermore, the longitudinal end portions 10ea and 10eb of the absorbent main body 10 (that is, the front upper end portion 10ea and the back upper end portion 10eb in the pants-shaped state) are respectively joined and fixed to nearest band members 31 and 41. Thus, its appearance is substantially an H shape as viewed from above. From this state, the diaper 1 is two-folded along a folding position which is the predetermined longitudinal position CL1 of the absorbent main body 10 (the longitudinal center position CL1 of the diaper 1). In the band members 31 and 41 facing each other in the foregoing two-folded state, the left-right-direction end portions 31e and 41e are joined by the foregoing side seal portion SS. Consequently, the band members 31 and 41 are connected in an annular shape, forming a pants-shaped diaper 1 in which a waist opening BH and a pair of leg openings LH and LH as shown in FIG. 2.

The absorbent main body 10 in the opened state shown in FIG. 2 has substantially a rectangular shape as viewed from above. the absorbent main body 10 is arranged so that its longitudinal direction extends along the longitudinal direction of the diaper 1. As shown in FIG. 3, the absorbent main body 10 includes: an absorbent body 11; a liquid-permeable top sheet 13 covering the absorbent body 11 from the skin side and serving as the skin-side surface of the absorbent main body 10; and a liquid-impermeable back sheet 15 covering the absorbent body 11 from the non-skin side and serving as the non-skin-side surface of the absorbent main body 10.

The absorbent body 11 includes a liquid-absorbent absorbent core 11c and a core-wrapping sheet (not shown) wrapping the outer surface of the absorbent core 11c. The absorbent core 11c is constituted by liquid-absorbent material (e.g., pulp fiber and super absorbent polymer) formed in a substantially hourglass shape as viewed from above; the substantially hourglass shape is an example of a predetermined shape. As the core-wrapping sheet, a liquid-permeable sheet such as tissue paper or nonwoven fabric can be employed, but core-wrapping sheet is not essential. Further, the shape of the absorbent core 11c is not limited to the foregoing substantially hourglass shape as viewed from above, and may be other shape.

The top sheet 13 is a liquid-permeable flexible sheet made of nonwoven fabric or the like. The back sheet 15 is a liquid-impermeable flexible sheet. The back sheet 15 is exemplified by a two-layered, laminated sheet composed of a liquid-impermeable leak-proof sheet (e.g., polyethylene film or polypropylene film) and an exterior sheet made of nonwoven fabric which is attached to the non-skin side of the leak-proof sheet.

As shown in FIG. 2, the back sheet 15 has at least a planar size in which the sheet 15 protrudes beyond the absorbent body 11 in the longitudinal direction and in the left-right direction. In each of the portions protruding in the left-right direction, a leg gather LG is formed which stretches/contracts in the longitudinal direction. Specifically, in the protruding portions, as elastic members, elastic strings 17 extending along the longitudinal direction are fixed with stretching in the longitudinal direction. Thus, the leg gathers LG having a stretch/contraction ability are formed in the portions.

As shown in FIGS. 2 and 3, for preventing side leakage, the absorbent main body 10 has barrier cuffs LSG and LSG on its end portions in the left-right direction, as leakage-proof walls. Specifically, elastic strings 18 with stretching in the longitudinal direction are attached as elastic members to a sheet portion which is to be the barrier cuff LSG, along the longitudinal direction. Furthermore, such a configuration is provided on each end portion of the absorbent main body 10 in the left-right direction.

Figure 4:
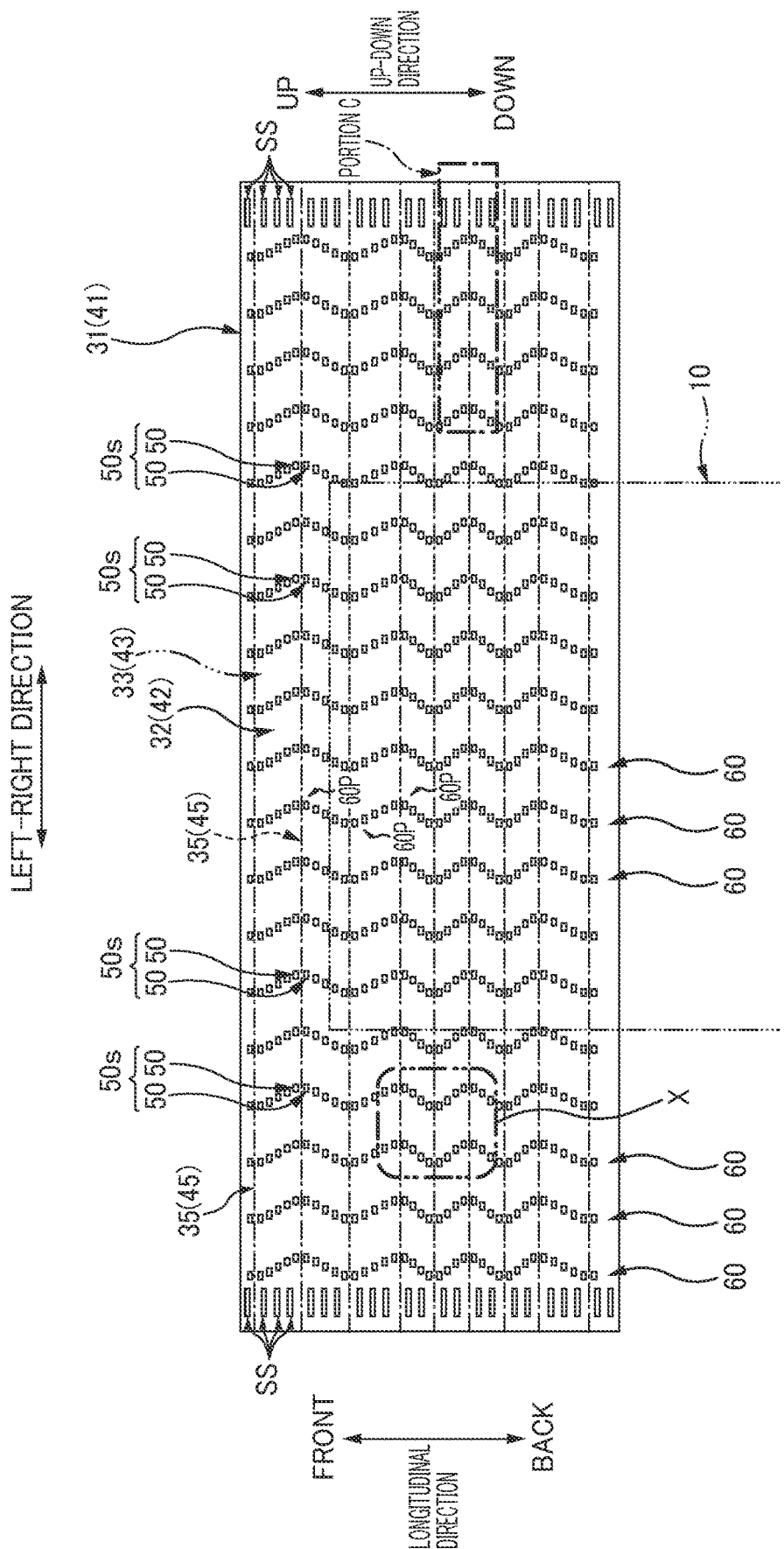
FIG. 4 shows a schematic plan view of a front band member 31 which is opened and stretched, as viewed from the non-skin side according to one or more embodiments.

As shown in FIG. 2, the front band member 31 is made of a first sheet 32 and a second sheet 33 which are stacked in the thickness direction and is a sheet member having a substantially rectangular shape as viewed from above. Specifically, as shown in FIG. 3, the first sheet 32 and the second sheet 33 are stacked in the thickness direction, and a pair of surfaces facing each other are joined by a plurality of welded portions 50, 50, . . . (corresponding to the joining portion) arranged discretely in the up-down direction and in the left-right direction as shown in FIG. 4 (to be described later). As shown in FIG. 2, the front band member 31 is arranged protruding beyond the absorbent main body 10 toward the sides in the left-right direction, and the front band member 31 is stacked on and joined to the front-side end portion (the front upper end portion) 10ea of the absorbent main body 10 from the non-skin side.

Similar to the front band member 31, the back band member 41 is made of a first sheet 42 and a second sheet 43 which are stacked in the thickness direction and is a sheet-like member having a substantially rectangular shape as viewed from above. Specifically, as shown in FIG. 3, the first sheet 42 and the second sheet 43 are stacked in the thickness direction, and a pair of surfaces facing each other are joined by a plurality of welded portions 50, 50, . . . (corresponding to the joining portion) arranged discretely in the up-down direction (the longitudinal direction) and in the left-right direction in the same manner as the front band member 31 shown in FIG. 4. As shown in FIG. 2, the back band member 41 is arranged protruding beyond the absorbent main body 10 toward the sides in the left-right direction, and the back band member 41 is stacked on and joined to the back-side end portion (the back upper end portion) 10eb of the absorbent main body 10 from non-skin side.

In this example, the first sheet 32 (42) and the second sheet 33 (43) for the front band member 31 (the back band member 41) both are made of spun-bonded nonwoven fabric. However, the present invention is not limited thereto. Other types of nonwoven fabric such as SMS (spun-bonded/melt-blown/spun-bonded) nonwoven fabric may be employed. In this example, single fiber made of polypropylene (PP), a typical thermoplastic resin, is used as constituent fiber of nonwoven fabric. However, the present invention is not limited thereto. For example, single fiber made of other thermoplastic resin such as polyethylene (PE) may be used, and composite fiber having a core-sheath structure of PE and PP may be used.

<Front Band Member 31>

A concrete structure of the front band member 31 and the back band member 41, which are stretchable/contractible sheets according to one or more embodiments will be described below. As mentioned above, the front band member 31 and the back band member 41 have substantially identical structures. Accordingly, in the following description, concerning things common to both of the front band member 31 and the back band member 41, only those of the front band member 31 will be described as a representative. Concerning the back band member 41, reference signs of its components corresponding to those of the front band member 31 will be indicated by blanketing as necessary, and the concrete description will be omitted.

FIG. 4 is a schematic plan view of the front band member 31 (stretchable/contractible sheet) which is opened and stretched, as viewed from the non-skin side. In FIG. 4, the front band member 31 (41) is shown as a component of the diaper 1, and the band members 31 and 41 can be applied, as a stretchable/contractible sheet, to other than the diaper 1. That is, FIG. 4 is a diagram showing a basic configuration of a stretchable/contractible sheet according to one or more embodiments.

As shown in FIG. 4, in the first sheet 32 (42) and the second sheet 33 (43) for the front band member 31 (41), a plurality of elastic members 35, 35, . . . (45, 45, . . . ) such as elastic strings are placed interposing between the pair of surfaces facing each other and aligning with a space in the up-down direction; the elastic members 35 are capable of stretching/contracting in the left-right direction. The elastic members 35 are attached to the sheets 32 and 33 (42 and 43) by the foregoing welded portions 50, 50 . . . . Accordingly, an ability to stretch/contract in the left-right direction is applied to the front band member 31 (41). That is, the welded portions 50, 50, . . . have not only a function to join the pair of facing surfaces the first sheet 32 (42) and the second sheet 33 (43), but also has a function to attach the elastic members 35 (45) to the first sheet 32 (42) and the second sheet 33 (43).

In the front band member 31 (41) of one or more embodiments, the plurality of welded portions 50, 50, . . . is arranged side-by-side in the up-down direction, forming the welded-portion row 60 extending along the up-down direction. A plurality of welded-portion rows 60 is provided with spaces in the left-right direction. Each of the welded-portion rows 60 is arranged so as to have convex portions 60P each of which protrudes toward the one side or the other side in the left-right direction, and is not arranged straight along the up-down direction. that is, the plurality of welded portions 50 included in the welded-portion row 60 is located at different positions in the left-right direction, forming the welded-portion row 60 so that the row 60 has convex portions and concave portions throughout the entire length. In the example of FIG. 4, the welded-portion row 60 is formed extending downward in the up-down direction so as to meander leftward and rightward. However, the arrangement of the welded portions 50 is not limited to the example of FIG. 4, and a configuration may be employed in which the welded-portion rows 60 have the convex portions 60P on only the one side in the left-right direction.

The plurality of welded portions 50 provided with a predetermined space in the up-down direction and in the left-right direction makes it possible to suppress deterioration of touch of the diaper 1 that is worn while maintaining the flexibility of the front band member 31 (41). Assuming that a line-shaped welded portion extending lengthwise (continuously) in the up-down direction or in the left-right direction is formed. In a portion where the welded portion is formed, nonwoven fabric becomes hard. It is more likely to suppress deformation of nonwoven fabric in a direction in which the line-shaped welded portion extends. In contrast, in one or more embodiments, since small welded portions are arranged discretely, it is possible to provide a flexible sheet member which makes it difficult for a user of the diaper 1 (a wearer) to feel curing of nonwoven fabric, and which makes it difficult to suppress deformation of nonwoven fabric in the up-down direction and in the left-right direction. The detail will be described later. Since the welded-portion row 60 are formed so as to have convex portions and concave portions in the left-right direction, irregular-shaped creases are more likely to be formed on the surface of the front band member 31 (41), making softer the touch of the diaper 1 when it is worn.

Figure 5A:
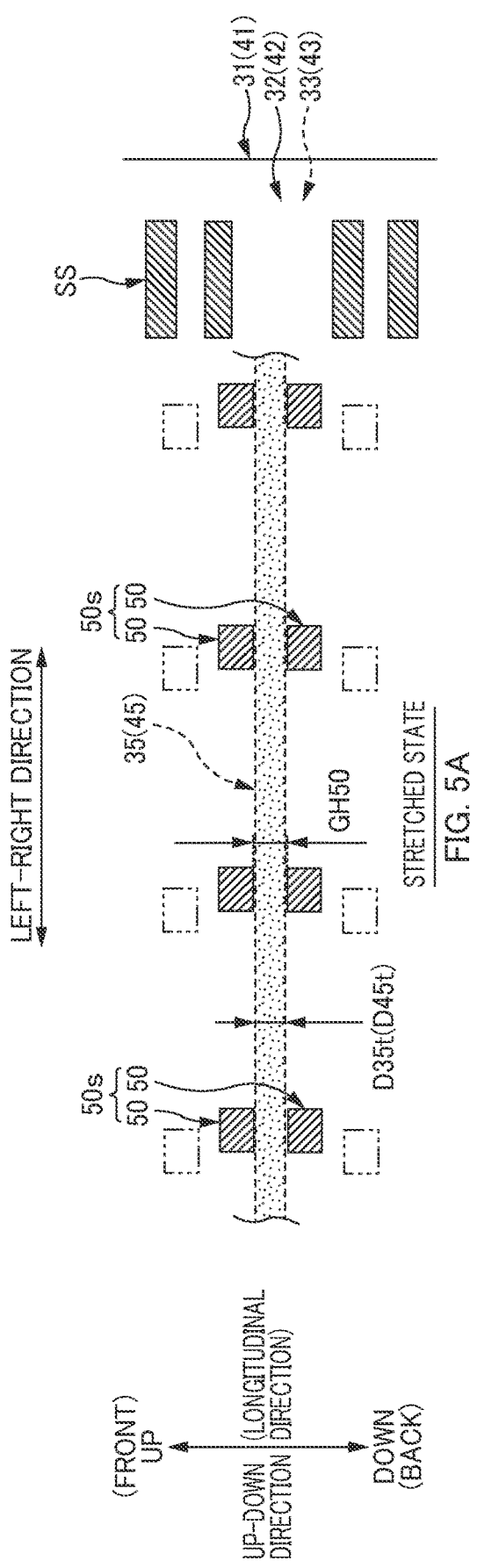
FIGS. 5A and 5B show diagrams showing a function to attach an elastic member 35, and are magnified view of the portion C in FIG. 4 according to one or more embodiments.
Figure 5B:
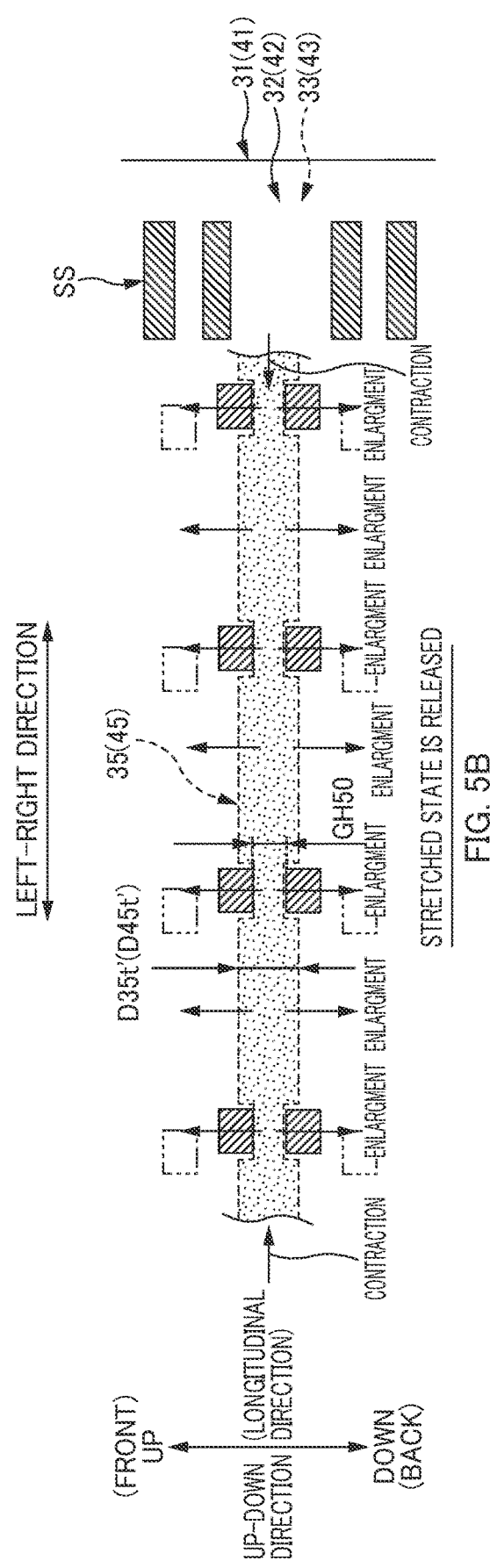

In the front band member 31 (41), an elastic member 35 is sandwiched in the up-down direction between two welded portions 50 and 50 adjacent (adjacent to each other) in the up-down direction, among the plurality of welded portions 50 in the welded-portion row 60; and thereby that elastic member 35 is attached to the front band member 31 (41). Specifically, a pair of welded portions 50 and 50 respectively located on both sides of the elastic member 35 in the up-down direction serve as a welded portion pair 50S, and the elastic member 35 is attached by the welded portion pair 50S. FIGS. 5A and 5B are diagrams showing a function to attach an elastic member 35, and are magnified view of the portion C in FIG. 4.

As shown in FIG. 5A, a pair of welded portions 50 and 50 constituting a welded portion pair 50S are placed side-by-side with a space GH50 in the up-down direction. The size (width) of the space GH50 is set to be equal to or slightly larger than the outer diameter D35$t$ (D45$t$) of the elastic member 35 (45) which is stretched at a target stretching ratio in the left-right direction (GH50≧D35$t$); the elastic member 35 (45) is an elastic string, for example. That is, the elastic member 35 in the stretched state is arranged between a welded portion pair 50S in the up-down direction. With such a configuration, in the production processes of the diaper 1 (the front band member 31), after arranging each of elastic members 35 between the first sheet 32 and the second sheet 33 while each of elastic members 35 is stretched, when welding the first sheet 32 and the second sheet 33, it is possible to form the welded portion 50 without overlapping the elastic members 35.

When the elastic member 35 (45) is released from the stretched state, the elastic member 35 (45) enlarges in the up-down direction with contracting in the left-right direction, and its outer diameter D35$t'$ after the enlarging is larger than the space GH50 of the welded portion pair 50S in the up-down direction (D35$t'$>GH50), as shown in FIG. 5B. Accordingly, enlarging of the elastic member 35 (45) in the up-down direction is restricted between the welded portion pair 50S, and thus the elastic member 35 (45) is substantially sandwiched between the welded portions 50 and 50 in the up-down direction. Consequently, the elastic member 35 (45) is attached to the front band member 31 (41). In the pants-shaped diaper 1 of FIG. 1, the elastic members 35 (45) are released from the stretched state. In the pants-shaped diaper 1, since the elastic members 35 are joined by the side seal portions SS in both left and right end portions 31$e$ of the front band member 31, the elastic members 35 will not be removed from the front band member 31 even if the front band member 31 (the elastic members 35) are stretched in the left-right direction when putting on the diaper 1.

Meanwhile, the foregoing stretching ratio is a value R indicating how many times longer the entire length L1 of the elastic member 35 (45) the original entire length L0 of the elastic member 35 (45) is (=L1/L0); the entire length L0 is a length in a state in which no force is exerted.

Figure 6:
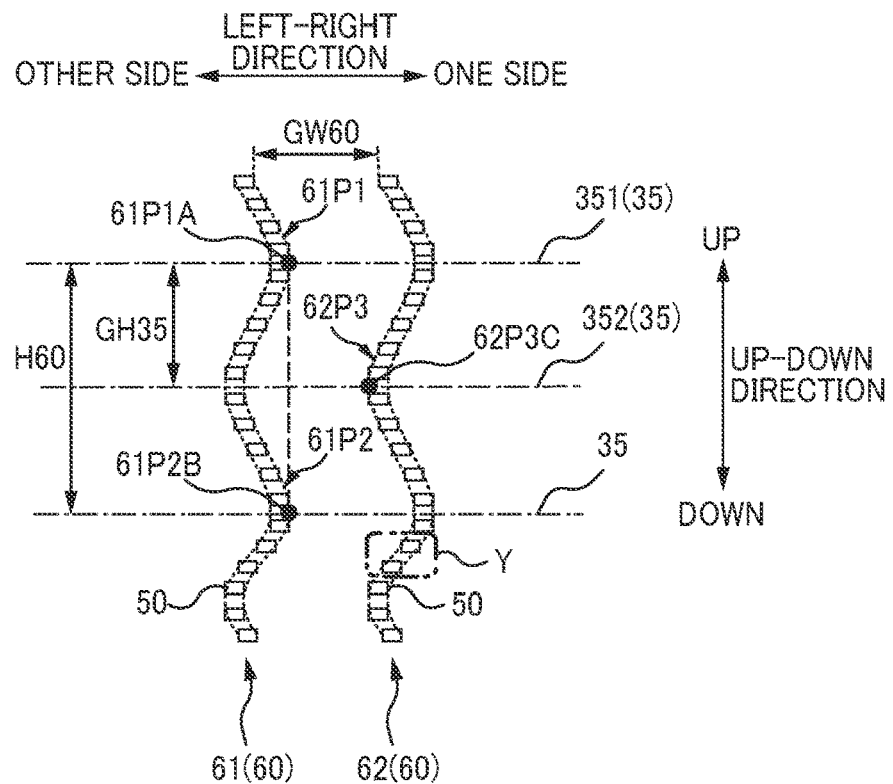
FIG. 6 shows a magnified view of a region X, and illustrates arrangement of welded-portion rows 60 when the welded-portion rows 60 are stretched in the left-right direction according to one or more embodiments.
Figure 7:
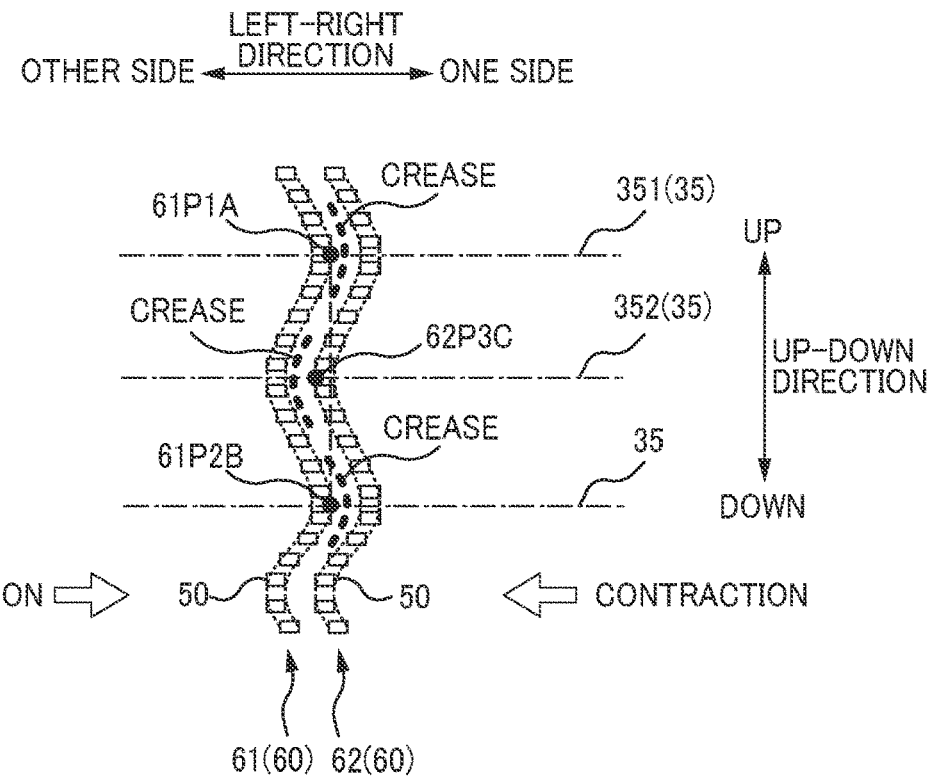
FIG. 7 shows a diagram illustrating arrangement of welded-portion rows 60 when the welded-portion rows 60 are in the natural state by being released (when the welded-portion rows 60 are released) from the stretched state according to one or more embodiments.
Figure 8:
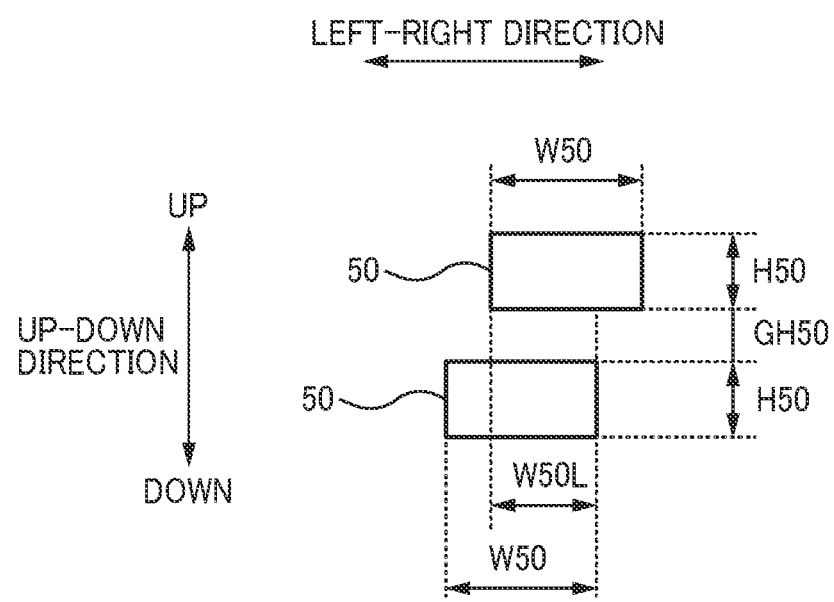
FIG. 8 shows a magnified view of the region Y shown in FIG. 6, and illustrates a positional relation of welded portions 50 according to one or more embodiments.

FIG. 6 is a magnified view of the region X shown in FIG. 4, and illustrates arrangement of welded-portion rows 60 when the welded-portion rows 60 are stretched in the left-right direction. FIG. 7 is a diagram illustrating arrangement of welded-portion rows 60 when the welded-portion rows 60 are in natural (non-stretched) state when the welded-portion rows 60 are released from the stretched state shown in FIG. 6. FIG. 8 is a magnified view of the region Y shown in FIG. 6, and illustrates a positional relation between welded portions 50 and 50 which are adjacent in the up-down direction.

The "natural state" is a state in which the diaper 1 or the front band member 31 (41) has been left for a certain period of time, or a state in which a stretchable and contractible sheet is not stretched in the left-right direction. For example, the front band member 31 and the back band member 41 of the diaper 1 are pulled outwardly toward both sides in the left-right direction, making the band members 31 and 41 be "stretched". Then, the stretched state continues for 15 seconds. Thereafter, the diaper 1 is released from being pulled and is placed on a flat surface such as a table. Thus, a state after the diaper 1 has been placed in such a manner in five minutes is defined as a natural state.

FIGS. 6 and 7 show a first welded-portion row 61 and a second welded-portion row 62; the second welded-portion row 62 is arranged adjacent to the first welded-portion row 61 and on the one side (right side in FIG. 6) in the left-right direction. The first welded-portion row 61 and the second welded-portion row 62 are each constituted by a plurality of welded portions 50 arranged side-by-side in the up-down direction as mentioned above. The first welded-portion row 61 and the second welded-portion row 62 each have convex portions and concave portions in the left-right direction. Specifically speaking, the first welded-portion row 61 includes: a first convex portion 61P1 protruding on the one side (right side) in the left-right direction; and a second convex portion 61P2 arranged adjacent to and below the first convex portion 61P1 in the up-down direction, and protruding on the one side (right side) in the left-right direction. Similarly, the second welded-portion row 62 includes a third convex portion 62P3 protruding on other side (other-side, or left side) in the left-right direction. The third convex portion 62P3 is located in the up-down direction between the first convex portion 61P1 and the second convex portion 61P2.

The shape of each welded portion 50 constituting the welded-portion rows 61 and 62 is a laterally elongated rectangle, as shown in FIG. 8, in which the length W50 in the left-right direction is larger than the length H50 in the up-down direction (W50>H50). As mentioned above, in one or more embodiments, in the natural state, the elastic member 35 is attached by vertically sandwiched between a pair of welded portion pair 50S adjacent in the up-down direction. Accordingly, shaping the welded portion 50 in a laterally elongated rectangle increases the area (length) in which the elastic member 35 and the welded portion pair 50S are in contact with each other in the left-right-direction. By this increase, friction force in the left-right direction increases, making it easier to fix the elastic member 35. However, the shape of the welded portion 50 is not limited to a laterally elongated rectangle shown in FIG. 8. For example, the welded portion 50 may have an elliptical shape or may have a longitudinally elongated shape. Further, each of the plurality of welded portions 50 may have different shapes. However, concerning two welded portions 50 constituting the welded portion pair 50S between which the elastic member 35 is vertically sandwiched, at least making the two welded portions 50 laterally elongated makes it possible to achieve an effect that displacement of the elastic member 35 is suppressed.

Concerning welded portions 50 and 50 of the welded-portion row 60 which are adjacent in the up-down direction, a space GH50 in the up-down direction between the welded portions 50 and 50 is smaller than the length H50 of the welded portion 50 in the up-down direction (H50>GH50). In one or more embodiments, in the natural state, for making it easier for creases to be formed in a region between adjacent welded-portion rows 60 and 60, each welded-portion row 60 does not have large break in the up-down direction. If the welded-portion row 60 has a large break in the up-down direction (that is, the space GH50 is large), distortion is more likely to be produced in the break at the time of contracting. Accordingly, in one or more embodiments, making smaller the space GH50 in the up-down direction between welded portions 50 and 50 than the length H50 suppresses large breakage of the welded-portion row 60 in the up-down direction. Consequently, in a region between welded-portion rows 60 and 60, distortion is less likely to be produced on the surface of the front band member 31 at the time of in the left-right-direction contraction of the front band member 31. This makes it easier to form creases along convex portions and concave portions (curves) of the welded-portion row 60.

As shown in FIG. 6, while the front band member 31 is stretched, the end 62P3C of the third convex portion 62P3 on the one side in the left-right direction is located on the one side (one-side, or right side) in the left-right direction, with respect to a straight line connecting the end 61P1A of the first convex portion 61P1 on the one side in the left-right direction and the end 61P2B of the second convex portion 61P2 on the one side in the left-right direction; The end 62P3C is the left side end of the third convex portion 62P3, the end 61P1A is the right side end of the first convex portion 61P1, and the end 61P2B is the right side end of the second convex portion 61P2.

In the natural state shown in FIG. 7, the end 62P3C of the third convex portion 62P3 on the one side in the left-right direction is located on the other side (left side) in the left-right direction, with respect to the straight line connecting the end 61P1A of the first convex portion 61P1 and the end 61P2B of the second convex portion 61P2. That is, when contraction of the elastic member 35 makes smaller the space between two welded-portion rows 60 adjacent in the left-right direction (the first welded-portion row 61 and the second welded-portion row 62 in FIGS. 6 and 7), the left side end 62P3C of the third convex portion 62P3 moves to the left side (the other side in the left-right direction) with respect to the right side end 61P1A of the first convex portion 61P1 (or the right side end 61P2B of the second convex portion 61P2). This makes it easier to form irregular creases between the first welded-portion row 61 and the second welded-portion row 62.

Figure 9A:
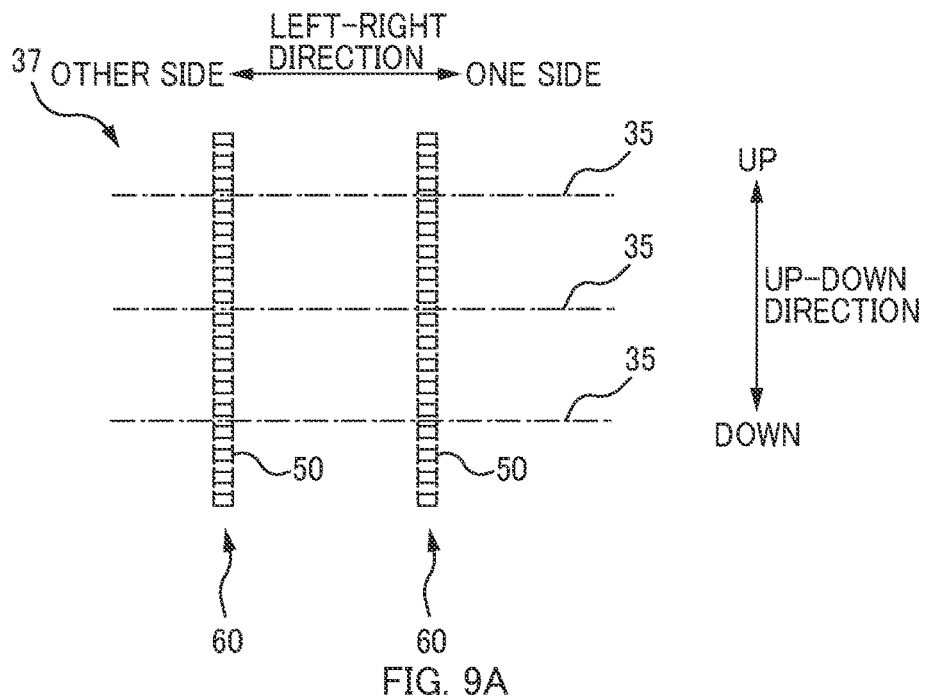
FIGS. 9A and 9B show diagrams illustrating formation of creases in a front band member 37 according to a comparative example according to one or more embodiments.
Figure 9B:
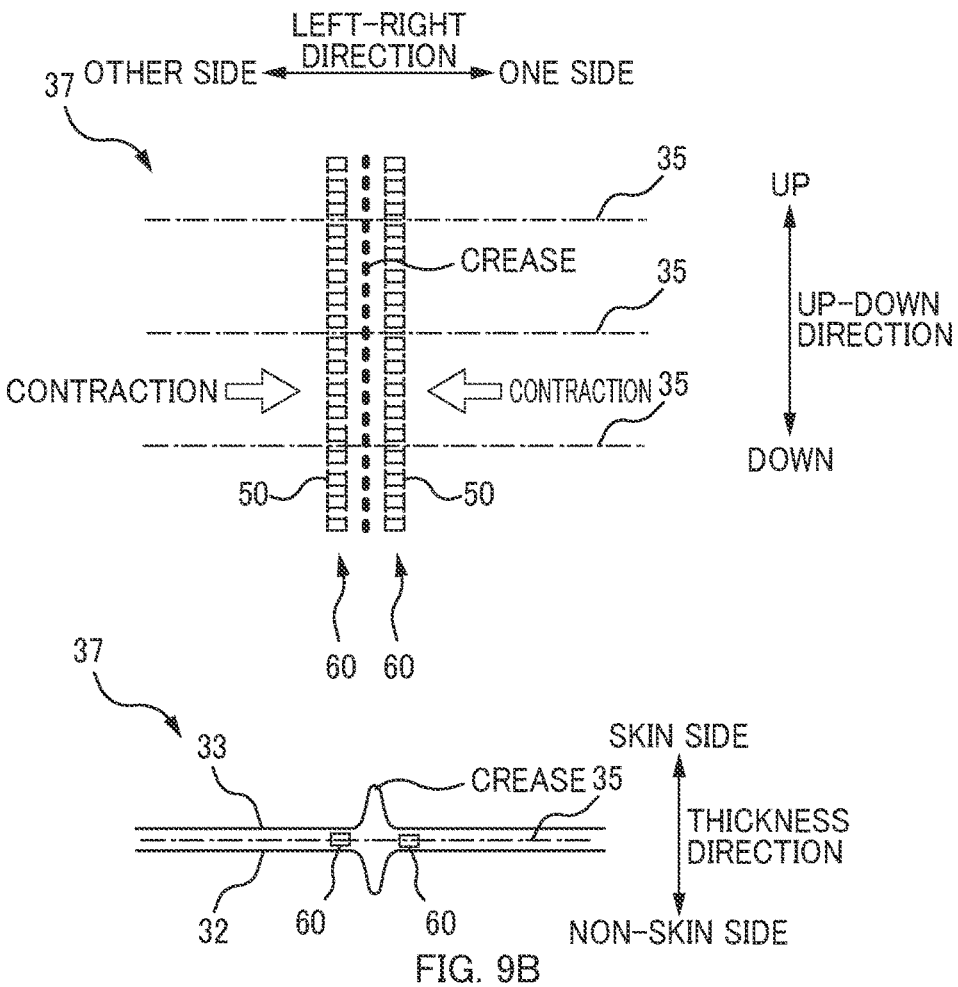

FIGS. 9A and 9B are diagrams illustrating formation of creases in a front band member 37 according to a comparative example. FIG. 9A corresponds to FIG. 6, and is a magnified view of a part of the welded-portion row 60 when the front band member 37 is stretched in the left-right direction. FIG. 9B corresponds to FIG. 7, and is a magnified view of a part of the welded-portion row 60 when the front band member 37 is in natural state. In the front band member 37 according to the comparative example, a plurality of welded portions 50, 50, ... is arranged side-by-side in the up-down direction, forming a welded-portion row 60 extending along the up-down direction. A plurality of welded-portion rows 60 is provided with a space in the left-right direction. But, each welded-portion row 60 does not include convex portions and concave portions which protrude in the left-right direction, or each welded-portion row 60 includes convex portions and concave portions which protrude slightly in the left-right direction. In the example of FIG. 9A, each welded-portion row 60 is formed extending straight along the up-down direction. The other basic configuration is the same as the front band member 31.

In the natural state, when the front band member 37 contracts in the left-right direction, as the space between two welded-portion rows 60 and 60 adjacent in the left-right direction becomes smaller, the nonwoven fabric (32, 33) between the welded-portion rows 60 and 60 rises upward in the thickness direction. Consequently, creases are formed shown by the thick dashed line of FIG. 9B. The creases extend in a straight, continuous manner along the up-down direction so as to be substantially parallel to the welded-portion rows 60. That is, in the front band member 37 of comparative example, long, large and regular creases are formed along the up-down direction. When a diaper including such a front band member 37 is worn, long straight creases are more likely to mark the wearer's skin, and pressure in edges of creases regularly formed is more likely to be exerted locally on the wearer's skin. Consequently, there is a risk of discomfort when the diaper is put on.

In contrast, in the front band member 31 according to one or more embodiments, in the natural state, the left side end 62P3C of the third convex portion 62P3 is located on the left side with respect to the right side end 61P1A of the first convex portion 61P1 (the right side end 61P2B of the second convex portion 61P2). Accordingly, straight creases in the comparative example are not formed, and irregular creases are more likely to be formed. Specifically, as shown by the thick dashed line of FIG. 7, curved creases meandering in the left-right direction (creases having a curvature) are formed between the first welded-portion row 61 and the second welded-portion row 62. The directions of the creases each differ with respect to the left-right direction, making it difficult to form crease s continuously elongated in the up-down direction. That is, a crease becomes more likely to be divided up and down around the middle in the left-right direction between a portion protruding toward the one side and a portion protruding toward the other side. This makes it easier to form creases finer than those of the comparative example (see FIG. 9B).

That is, in the front band member 31 (41) according to one or more embodiments, in the stretched state, the left side end 62P3C of the third convex portion 62P3 is located on the right side with respect to the right side end 61P1A of the first convex portion 61P1 (the right side end 61P2B of the second convex portion 61P2). In the natural state, moving the left side end 62P3C to the left side with respect to the right side end 61P1A of the first convex portion 61P1 (the right side end 61P2B of the second convex portion 61P2), making it possible to form irregular, fine creases. Accordingly, when a diaper including such a front band member 31 is worn, long straight creases are less likely to mark the wearer's skin, and it is possible for the wearer to feel good touch because the creases irregularly formed distribute pressure. In a portion where such fine creases are formed, the basis weight (weight per unit area) of the sheet member (nonwoven fabric) is locally large, increasing cushioning of the sheet member. This makes for the elastic members 35 difficult to be jammed into the wearer's skin in the portion where the creases are formed, making it possible to realize better touch.

In the front band member 31 (41), each of the plurality of welded portions 50 constituting the welded-portion row 60 is arranged so that each pair of two welded portions 50 and 50 adjacent in the up-down direction has a portion overlapping in the left-right direction. In FIG. 8, of the welded portion 50 having the length W50 in the left-right direction, a portion having the length W50L overlaps a welded portion 50 adjacent in the up-down direction. That is, each welded portion 50 is formed so that the displacement in the left-right direction between each pair of two welded portions 50 and 50 adjacent in the up-down direction is smaller than the length W50. For example, if displacement in the left-right direction between the welded portions 50 and 50 is larger than the length W50 of the welded portion 50 in the left-right direction, the welded-portion row 60 has a zig-zag shape. In this case, creases formed in a region between welded-portion rows 60 and 60 is also more likely to have a zig-zag shape composed of straight lines, making it difficult to realize soft touch. In contrast, in one or more embodiments, displacements of the welded portions 50 in the left-right direction are restricted, and it makes it easier to form fine, smoothly-curved creases shown in FIG. 7. Consequently, it is possible to realize soft touch of the front band member 31.

Further, each welded portion 50 is arranged so that the length W50L of the left-right-direction overlapping portion of two welded portions 50 and 50 adjacent in the up-down direction is larger than the length (W50−W50L) of the not-overlapping portion. That is, the length W50L of the overlapping portion of the welded portions 50 is larger than half the length W50 of each welded portion 50 in the left-right direction (W50L>0.5×W50). This prevents the left-right-direction amplitude of the convex portions and concave portions of the welded-portion row 60 from being excessively large, making it easier for the welded-portion row 60 to be in a form of smooth curves as shown in FIG. 4. This makes it easier to form irregular, fine creases having smooth curves between left-right adjacent welded-portion rows 60 and 60, and makes it possible to realize softer touch.

Making the left-right-direction displacement (W50−W50L) of two welded portions 50 and 50 adjacent in the up-down direction as small as possible can form the welded-portion row 60 having a shape smoothly meandering in the left-right direction. This makes it easier to form the foregoing curved fine creases. Also, this makes it possible for the welded-portion row 60 itself to form curved geometric pattern on the surface of the front band member 31 (41), improving appearance design of the front band member 31 (41).

In the front band member 31 (41), the elastic members 35 are arranged so that the up-down-direction pitch between at least some of elastic members 35 is smaller than the distance between the peaks of two adjacent-in-up-down-direction convex portions of a welded-portion row 60. In the example of FIG. 6, the space GH35 is smaller than the distance H60 (H60>GH35): the distance H60 is the up-down-direction distance between the right side end 61P1A of the first convex portion 61P1 and the right side end 62P2B of the second convex portion 61P2; and the space GH35 is the up-down-direction space between a first elastic member 351 and a second elastic member 352 that is arranged adjacent to and below the first elastic member 351 in the up-down direction.

As mentioned above, in the front band member 31 (41), the left-right-direction contractions of the elastic members 35 (45) form fine creases in a region between adjacent-in-up-down-direction convex portions 60P and 60P of the welded-portion row 60, realizing good touch. Accordingly, if the contraction force caused by the elastic members 35 is not sufficiently exerted on the region, there is a risk that creases are less likely to be formed. For this reason, in one or more embodiments, in at least a part of each welded-portion row 60, the up-down-direction space (pitch) of the elastic members 35 is smaller than the space (pitch) of convex portions adjacent in the up-down direction. This may enable the left-right-direction contraction force to be exerted on the region between the convex portions, making it easier to form creases. This makes it easier to realize good touch.

Further, in the front band member 31 (41), the up-down-direction pitch of the elastic members 35 is smaller than length half the distance between the peaks of two adjacent-in-up-down-direction convex portions of the welded-portion row 60. For example, in FIG. 6, the length half the distance H60 is larger than the space GH35 (0.5×H60>GH35): the distance H60 is the up-down-direction distance between the right side end 61P1A of the first convex portion 61P1 and the right side end 61P2B of the second convex portion 61P2; and the space GH35 is the up-down-direction space between the first elastic member 351 and the second elastic member 352 that is arranged adjacent to and below the first elastic member 351 in the up-down direction. Such a configuration makes the elastic members 35 exert a greater per-unit-area contraction force on the region between the convex portions 60P and 60P adjacent in the up-down direction. This can make it easier to form creases.

The elastic members 35 are attached to the front band member 31 with being stretched at a predetermined stretching ratio, and the elastic members 35 are released from the stretched state and contract. Thus, the front band member 31 has stretch/contraction ability. In the natural state shown in FIG. 7, the left side end 62P3C of the third convex portion 62P3 moves on the left side with respect to the right side end 61P1A of the first convex portion 61P1 (the right side end 61P2B of the second convex portion 61P2), making it possible to form irregular, fine creases. Accordingly, in one or more embodiments, there is a straight line connecting the right side end 61P1A of the first convex portion 61P1 and the right side end 61P2B of the second convex portion 61P2, and the elastic members 35 are attached to the front band member 31 (the first and second sheets 32 and 33) at a stretching ratio that produces the following contraction force; the contraction force is capable of moving, with respect to the foregoing straight line, the left side end 62P3C of the third convex portion 62P3 from the right side in the left-right-direction stretched state to the left side in the natural state. Attaching elastic members 35 at such a stretching ratio can make it easier to form irregular, fine creases on the surface of the front band member 31.

A specific stretching ratio for attaching the elastic members 35 may not be less than twice and not more than third times. In the case where the stretching ratio is less than twice, sufficient contraction force does not produce. In this case, the left side end 62P3C of the third convex portion 62P3 in the natural state sometimes cannot move to the left side with respect to the straight line connecting the right side end 61P1A of the first convex portion 61P1 and the right side end 61P2B of the second convex portion 61P2. On the other hand, in the case where the stretching ratio is more than third times, the contraction force becomes excessively great. This increases tightness around the waist of a wearer of the diaper 1, making it easier for the wearer to feel discomfort. In one or more embodiments, the stretching ratio for attaching the elastic members 35 is set within a range not less than twice and not more than third times, and this ensures proper left-right-direction contraction of the front band member 31, making it possible to realize both good fit and good touch when the diaper 1 is put on.

In one or more embodiments, a space GW60 between two welded-portion rows 60 and 60 adjacent in the left-right direction (in FIG. 6, the distance in the left-right direction between the right side end of the first welded-portion row 61 and the left side end of the second welded-portion row 62) is less than or equal to 6 mm. If the space GW60 is too large, even when the stretching ratio of the elastic members 35 is within a range from twice to third times as mentioned above, the left side end 62P3C of the third convex portion 62P3 in the natural state sometimes cannot move to the left side with respect to the straight line connecting the right side end 61P1A of the first convex portion 61P1 and the right side end 61P2B of the second convex portion 61P2. In this case, there is a risk that long, continuous and straight creases along the up-down direction shown in FIG. 9B are formed. In contrast, if the space GW60 is not more than 6 mm, in the natural state, the left side end 62P3C of the third convex portion 62P3 is easy to move to the left side with respect to the straight line connecting the right side end 61P1A of the first convex portion 61P1 and the right side end 61P2B of the second convex portion 61P2. This makes it possible to form irregular, fine creases on the surface of the front band member 31.

As mentioned above, if the waist member of an absorbent article such as a diaper 1 is the front band member 31 (41) having the foregoing features, it is possible to achieve good touch and good fit. In the front band member 31 (41), creases bent in the left-right direction are formed along the welded-portion rows 60, and such creases are less likely to crush than straight creases shown in FIG. 9B. Specifically, between the welded-portion rows 60 and 60 adjacent in the left-right direction, nonwoven fabric (the first sheet 32 and the second sheet 33) rises upward on the skin side and the non-skin side in the thickness direction, and creases are formed. When such creases are formed straight, at a time when the creases are pushed against wearer's skin folds are formed at the bases of the rising, and the creases become more likely to fall (crush). However, in one or more embodiments, since creases are formed in a curved manner, creases are less likely to fall (crush) than straight creases. This makes it easier to keep good fit and/or good touch when the diaper 1 is put on.

The pitch (GH35) of the elastic members 35 of the front band member 31 in the up-down direction is different from the pitch of the elastic members 45 of the back band member 41 in the up-down direction. If the pitches in the up-down direction are different between the elastic members 35 and the elastic members 45, contraction force exerted by the elastic members on unit area becomes different between the front band member 31 and the back band member 41. Accordingly, the size and the shape of creases formed at the time of contracting can be different between the front side and the back side of the diaper 1. Since the size and the shape of creases formed on each surface are different, the front band member 31 and the back band member 41 are less likely to be in close contact in the thickness direction, making it easier to handle the diaper 1. For example, at the time of shipping the diaper 1 from its manufacturing plant, the front band member 31 and the back band member 41 are compressed and packed with being stacked in the thickness direction. When a user (purchaser) uses the diaper 1, he or she has to open the front band member 31 and the back band member 41 in the front-back direction to form its waist opening (see FIG. 1). At this occasion, the user is easy to open the waist opening because the front band member 31 and the back band member 41 are not in close contact with each other.

Further, in one or more embodiments, the pitch of the elastic members 45 of the back band member 41 in the up-down direction is larger than the pitch (GH35) of the elastic members 35 of the front band member 31 in the up-down direction. The wider the pitch between elastic members in the up-down direction is, the larger the inclination of creases formed at the time of contracting (the inclination with respect to the left-right direction) is, making it easier to form creases whose inclinations are large in the back band member 41. Stretching creases having large inclinations, in a straight manner along the up-down direction makes it possible to stretch the back band member 41 in the up-down direction. That is, by the amount the inclinations of creases are large in the back band member 41, the back band member 41 has a longer elongation in the up-down direction than that of the front band member 31. Consequently, when putting on the diaper 1, the back band member 41 becomes easier to stretch in the up-down direction than the front band member 31 do. Accordingly, in the region of buttocks whose movement is large, the back band member 41 stretches in the up-down direction following the wearer's body movement, making it easier to suppress deterioration of fit.

While embodiments are described above, the above-mentioned embodiments are provided for facilitating the understanding, and are not to be interpreted as limiting the present invention. As a matter of course, the present invention can be altered and improved without departing from the gist thereof and the present invention includes equivalent thereof. For example, one or more embodiments can be altered as described below.

In one or more embodiments, it is not necessary that the side seal portions SS are rectangle. Not only a rectangle, but also any type of shape such as an ellipse, a circle, and a parallelogram may be employed. In addition, it is not necessary that the side seal portions SS are composed of a plurality of side welded portions SS arranged with spacing in the up-down direction. For example, according to one or more embodiments, a side seal portion SS extending from the upper end to the lower end may be provided on each of the end portions of the diaper 1 in the left-right direction.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1 diaper (absorbent article, disposable diaper),
10 absorbent main body,
10ea end portion, 10eb end portion,
11 absorbent body, 11c absorbent core,
13 top sheet, 15 back sheet,
17 elastic string, 18 elastic string,
31 front band member, 31e end portion,
32 first sheet, 33 second sheet,
35 elastic member, 351 first elastic member, 352 second elastic member,
37 front band member (comparative example)
41 back band member, 41e end portion,
42 first sheet, 43 second sheet,
45 elastic member,
50 welded portion, 50S welded portion pair,
60 welded-portion row,
60P convex portion,
61 first welded-portion row, 61P1 first convex portion, 61P1A end, 61P2 second convex portion, 61P2B end,
62 second welded-portion row, 62P3 third convex portion, 62P3C end,
BH waist opening, LH leg opening,
CL1 center position,
LG leg gather,
LSG barrier cuff (leakage-proof wall)

What is claimed is:

1. An absorbent article having an up-down direction and a left-right direction intersecting each other, comprising:
   an absorbent main body that absorbs excrement;
   a front band member disposed along the left-right direction and joined to a front-upper-end portion of the absorbent main body; and
   a back band member disposed along the left-right direction separately from the front band member and joined to a back-upper-end portion of the absorbent main body, wherein the front band member and the back band member each comprise:
   a first sheet;
   a second sheet;
   a plurality of welded portions that joins the first sheet and the second sheet;
   a plurality of elastic members that is stretchable and contractible in the left-right direction;
   a first welded-portion row that comprises the plurality of welded portions arranged side-by-side in the up-down direction; and
   a second welded-portion row that comprises the plurality of welded portions arranged side-by-side in the up-down direction, and located adjacent to the first welded-portion row on a one side in the left-right direction,
   the plurality of elastic members is arranged with a space in the up-down direction and between the first sheet and the second sheet,
   each of the elastic members is sandwiched between two welded portions adjacent in the up-down direction with contracting in the left-right direction, and is attached to the first sheet and the second sheet,
   the first welded-portion row comprises:
   a first convex portion that protrudes toward the one side in the left-right direction and
   a second convex portion located adjacent to the first convex portion in the up-down direction,
   the second welded-portion row comprises a third convex portion that protrudes toward another side in the left-right direction,
   when the elastic members are not stretched in the left-right direction, an other-side end of the third convex portion is located closer to the another side than a straight line that connects a one-side end of the first convex portion and a one-side end of the second convex portion,
   when the elastic members are stretched in the left-right direction, the other-side end of the third convex portion is located closer to the one side than the straight line,
   an end portion of the front band member in the left-right direction is joined to an end portion of the back band member in the left-right direction by a first side seal portion,
   another end portion of the front band member in the left-right direction is joined to another end portion of the back band member in the left-right direction by a second side seal portion, the first welded-portion row is located between the first side seal portion and the second side seal portion in the left-right direction, and the second welded-portion row is located between the first side seal portion and the second side seal portion in the left-right direction.

2. The absorbent article according to claim 1, wherein of the plurality of welded portions included in the first welded-portion row and the second welded-portion row,
each pair of two welded portions adjacent in the up-down direction comprises a portion overlapping in the left-right direction.

3. The absorbent article according to claim 2, wherein a length of the portion that is included in the two welded portions adjacent in the up-down direction and in which the two welded portions overlap in the left-right direction is larger than
a length of a portion that is included in the two welded portions and in which the two welded portions do not overlap in the left-right direction.

4. The absorbent article according to claim 2, wherein the first welded-portion row and the second welded-portion row extend downward in the up-down direction and meanders in the left-right direction.

5. The absorbent article according to claim 1, wherein a length of the welded portion in the left-right direction is larger than a length of the welded portion in the up-down direction.

6. The absorbent article according to claim 1, wherein a length of the welded portion in the up-down direction is larger than an up-down-direction space of two adjacent welded portions.

7. The absorbent article according to claim 1, wherein the plurality of elastic members comprises a first elastic member and a second elastic member adjacent to the first elastic member in the up-down direction, and
a first space in the up-down direction between the first elastic member and the second elastic member is smaller than a second space in the up-down direction between the one-side end of the first convex portion and the one-side end of the second convex portion.

8. The absorbent article according to claim 7, wherein the first space is smaller than half the second space.

9. The absorbent article according to claim 1, wherein in the up-down direction,
a first space of the elastic members disposed in the front band member is different from a second space of the elastic members disposed in the back band member.

10. The absorbent article according to claim 9, wherein the first space is smaller than the second space.

11. An absorbent article having an up-down direction and a left-right direction intersecting each other comprising:
an absorbent main body that absorbs excrement;
a front band member disposed along the left-right direction and joined to a front-upper-end portion of the absorbent main body; and
a back band member disposed along the left-right direction separately from the front band member and joined to a back-upper-end portion of the absorbent main body, wherein the front band member and the back band member each comprise:
a first sheet;
a second sheet;
a plurality of welded portions that joins the first sheet and the second sheet;
a plurality of elastic members that is stretchable and contractible in the left-right direction;
a first welded-portion row that comprises the plurality of welded portions arranged side-by-side in the up-down direction; and
a second welded-portion row that comprises the plurality of welded portions arranged side-by-side in the up-down direction, and located adjacent to the first welded-portion row on a one side in the left-right direction,
the plurality of elastic members is arranged with a space in the up-down direction and between the first sheet and the second sheet,
each of the elastic members is sandwiched between two welded portions adjacent in the up-down direction with contracting in the left-right direction, and is attached to the first sheet and the second sheet;
the first welded-portion row comprises:
a first convex portion that protrudes toward the one side in the left-right direction; and
a second convex portion located adjacent to the first convex portion in the up-down direction,
the second welded-portion row comprises a third convex portion that protrudes toward another side in the left-right direction,
when the elastic members are not stretched in the left-right direction, an other-side end of the third convex portion is located closer to the another side than a straight line that connects a one-side end of the first convex portion and a one-side end of the second convex portion,
the elastic members are attached at a stretching ratio that produces a contraction force that is capable of moving the other-side end of the third convex portion so that:
when the elastic members are stretched in the left-right direction, the other-side end of the third convex portion is located closer to the one side than the straight line; and
when the elastic members are not stretched in the left-right direction, the other-side end of the third convex portion is located closer to the another side than the straight line,
an end portion of the front band member in the left-right direction is joined to an end portion of the back band member in the left-right direction by a first side seal portion,
another end portion of the front band member in the left-right direction is joined to another end portion of the back band member in the left-right direction by a second side seal portion,
the first welded-portion row is located between the first side seal portion and the second side seal portion in the left-right direction, and
the second welded-portion row is located between the first side seal portion and the second side seal portion in the left-right direction.

12. The absorbent article according to claim 11, wherein the elastic member is attached at a stretching ratio not less than twice and not more than third times.

13. The absorbent article according to claim 11, wherein in the left-right direction, a space of two adjacent welded portions is less than or equal to 6 mm.

14. The absorbent article according to claim 11, wherein in the up-down direction,
a first space of the elastic members disposed in the front band member is different from a second space of the elastic members disposed in the back band member.

15. The absorbent article according to claim 14, wherein the first space is smaller than the second space.

\* \* \* \* \*